(12) United States Patent
Müller et al.

(10) Patent No.: US 7,186,672 B2
(45) Date of Patent: Mar. 6, 2007

(54) FUNGICIDAL MIXTURES

(75) Inventors: Bernd Müller, Frankenthal (DE); Ingo Rose, Mannheim (DE); Eberhard Ammermann, Heppenheim (DE); Reinhard Stierl, Mutterstadt (DE); Gisela Lorenz, Hambach (DE); Siegfried Strathmann, Limburgerhof (DE); Maria Scherer, Landau (DE); Klaus Schelberger, Gönnheim (DE); Joachim Leyendecker, Hassloch (DE); Egon Haden, Kleinniedesheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/466,168

(22) PCT Filed: Jan. 17, 2002

(86) PCT No.: PCT/EP02/00411

§ 371 (c)(1),
(2), (4) Date: Jul. 14, 2003

(87) PCT Pub. No.: WO02/056686

PCT Pub. Date: Jul. 25, 2002

(65) Prior Publication Data

US 2004/0077700 A1     Apr. 22, 2004

(30) Foreign Application Priority Data

Jan. 18, 2001   (DE) ................................ 101 02 279
May 15, 2001   (DE) ................................ 101 23 734

(51) Int. Cl.
*A01N 25/26*     (2006.01)

(52) U.S. Cl. ...................................... 504/100; 504/139
(58) Field of Classification Search ................ 424/405; 504/100, 139
See application file for complete search history.

(56) References Cited

U.S. PATENT DOCUMENTS

| 5,824,705 | A | 10/1998 | Mueller et al. |
| 5,869,517 | A | 2/1999 | Mueller et al. |
| 6,180,638 | B1 | 1/2001 | Mueller et al. |
| 6,346,535 | B1 | 2/2002 | Cotter et al. |
| 6,689,776 | B2 * | 2/2004 | Dalton .................... 514/229.2 |

FOREIGN PATENT DOCUMENTS

| EP | 393746 | * 10/1990 |
| EP | 727 141 | 8/1996 |
| EP | 897 904 | 2/1999 |
| EP | 899 255 | 3/1999 |
| EP | 967 196 | 12/1999 |
| EP | 1 023 834 | 8/2000 |
| WO | 97/40688 | 11/1997 |
| WO | 00/76317 | 12/2000 |

* cited by examiner

*Primary Examiner*—Alton Pryor
(74) *Attorney, Agent, or Firm*—Novak Druce & Quigg LLP

(57) ABSTRACT

Fungicidal mixtures comprising
a) a benzophenone of the formula I,
b) a carbamate of the formula II, and
c) an azole derivative of the formula III in a synergistically effective amount, and a method for controlling harmful fungi using mixtures of the compounds I, II and III are described. The active compounds of the formulae I, II and III are defined in the description.

9 Claims, No Drawings

FUNGICIDAL MIXTURES

The present invention relates to fungicidal mixtures, comprising
a) a benzophenone of the formula I,

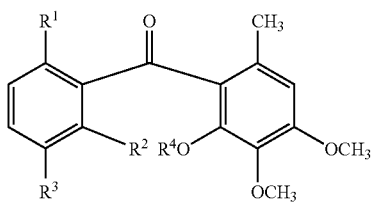

I in which
$R^1$ is chlorine, methyl, methoxy, acetoxy, pivaloyloxy or hydroxyl;
$R^2$ is chlorine or methyl;
$R^3$ is hydrogen, halogen or methyl; and
$R^4$ is $C_1$–$C_6$-alkyl or benzyl, where the phenyl moiety of the benzyl radical may carry a halogen or methyl substituent, and
b) a carbamate of the formula II,

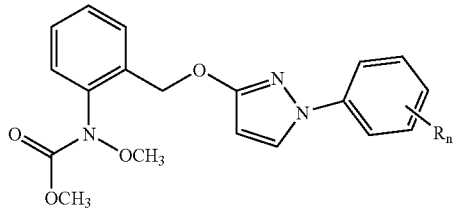

II in which n is 1 or 2 and R is halogen, $C_1$–$C_4$-alkyl or $C_1$–$C_2$-haloalkyl, where the radicals R may be different if n is 2, and
c) an azole derivative III selected from the group of the compounds III.a to III.e:
(2RS,3SR)-1-[3-(2-chlorophenyl)-2-(4-fluorophenyl)-oxiran-2-ylmethyl]-1H-1,2,4-triazole

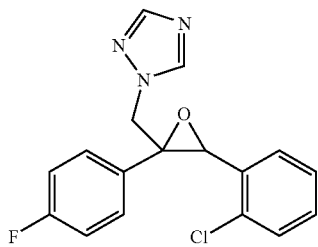

III.a (1RS,5RS;1RS,5SR)-5-(4-chlorobenzyl)-2,2-dimethyl-1-(1H-1,2,4-triazol-1-ylmethyl)cyclopentanol

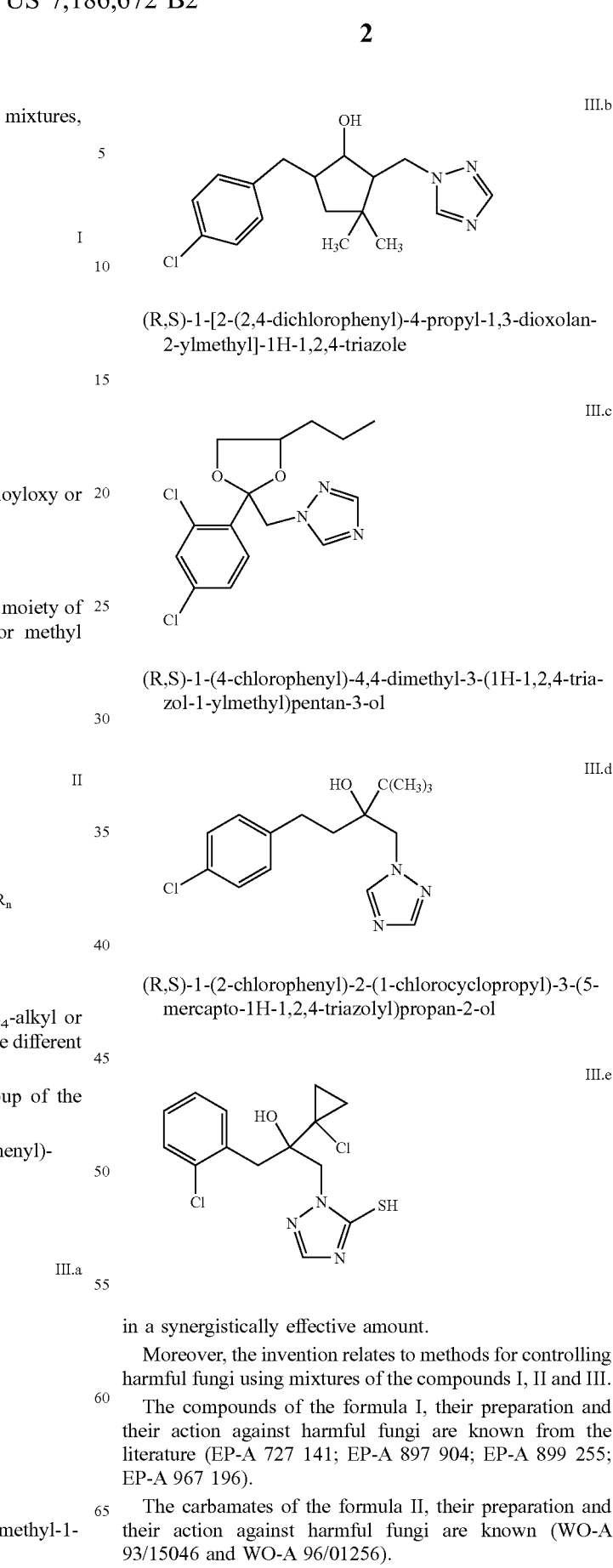

(R,S)-1-[2-(2,4-dichlorophenyl)-4-propyl-1,3-dioxolan-2-ylmethyl]-1H-1,2,4-triazole (R,S)-1-(4-chlorophenyl)-4,4-dimethyl-3-(1H-1,2,4-triazol-1-ylmethyl)pentan-3-ol (R,S)-1-(2-chlorophenyl)-2-(1-chlorocyclopropyl)-3-(5-mercapto-1H-1,2,4-triazolyl)propan-2-ol in a synergistically effective amount.

Moreover, the invention relates to methods for controlling harmful fungi using mixtures of the compounds I, II and III.

The compounds of the formula I, their preparation and their action against harmful fungi are known from the literature (EP-A 727 141; EP-A 897 904; EP-A 899 255; EP-A 967 196).

The carbamates of the formula II, their preparation and their action against harmful fungi are known (WO-A 93/15046 and WO-A 96/01256).

The azole derivatives of the formula III, their preparation and their action against harmful fungi are known to the person skilled in the art from the literature:

IIIa: common name: epoxiconazole, EP-A 196 038, CAS RN [106325-08-0];
IIIb: common name: metconazole, Proc. Br. Crop Prot. Conf.-Pests Dis., 5-4, 419 (1992), CAS RN [125116-23-6];
IIIc: common name: propiconazole, GB-A 1,522,657, CAS RN [60207-90-1];
IIId: common name: tebuconazole, EP-A 40345, CAS RN [107534-96-3];
IIIe: DE-A 198 29 075.

Binary mixtures of benzophenones of the formula I with azole derivatives of the formula III are known from EP-A 1 023 834.

Binary mixtures comprising carbamates of the formula II and azole derivatives of the formula III are known from EP-A 900 021.

A possible synergism between the specifically substituted benzophenones of the formula I and the carbamates of the formula II (see Table II) is postulated in WO-A 00/76317. However, this publication does not demonstrate any synergism.

It is an object of the present invention to provide mixtures which have a further improved activity against harmful fungi combined with a reduced total amount of active compounds applied (synergistic mixtures), with a view to reducing the application rates and improving the activity spectrum of the known compounds I, II and III and the known binary mixtures.

We have found that this object is achieved by the mixtures defined at the outset. Moreover, we have found that applying the compounds I, II and III simultaneously, i.e. together or separately, or applying the compounds I, II and III in succession provides better control of harmful fungi than is possible with the individual compounds or a binary mixture alone.

The following compounds of the formula I are preferred components of the mixture, the individual preferences applying on their own and in combination.

Preference is given to compounds I in which $R^1$ is chlorine, methoxy, acetoxy or hydroxyl, and particular preference is given to compounds in which $R^1$ is methoxy, acetoxy or hydroxyl. Very particular preference is given to compounds in which $R^1$ is methoxy.

Mixtures comprising compounds I in which $R^2$ is chlorine or methyl are mixtures according to the invention. Preference is given to compounds I in which $R^2$ is methyl.

Moreover, preference is given to compounds I in which $R^3$ is hydrogen, methyl, chlorine or bromine, particularly preferably hydrogen, chlorine or bromine.

In addition, preference is given to compounds I in which $R^4$ is $C_1$–$C_4$-alkyl or benzyl, where the phenyl moiety of the benzyl radical may carry a halogen or methyl substituent. Particular preference is given to compounds of the formula I in which $R^4$ is $C_1$–$C_4$-alkyl, preferably methyl.

Preference is furthermore given to compounds of the formula I in which the substituents $R^1$, $R^2$, $R^3$ and $R^4$ are as defined below:

$R^1$ is methoxy, acetoxy or hydroxyl;
$R^2$ is methyl;
$R^3$ is hydrogen, chlorine or bromine; and
$R^4$ is $C_1$–$C_4$-alkyl.

In addition, particular preference is given to compounds of the formula I in which the substituents have the meanings given in the table below:

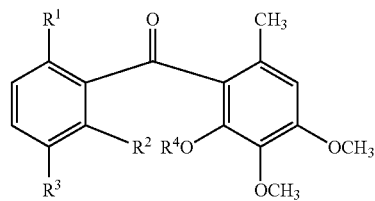

TABLE 1

| No. | $R^1$ | $R^2$ | $R^3$ | $R^4$ |
|---|---|---|---|---|
| I-1 | methoxy | Cl | H | methyl |
| I-2 | methoxy | Cl | methyl | methyl |
| I-3 | methoxy | Cl | H | n-propyl |
| I-4 | methoxy | Cl | H | n-butyl |
| I-5 | methoxy | Cl | H | benzyl |
| I-6 | methoxy | Cl | H | 2-fluorobenzyl |
| I-7 | methoxy | Cl | H | 3-fluorobenzyl |
| I-8 | methoxy | Cl | H | 4-fluorophenyl |
| I-9 | methoxy | Cl | H | 2-methylphenyl |
| I-10 | methoxy | Cl | H | 3-methylphenyl |
| I-11 | methoxy | Cl | H | 4-methylphenyl |
| I-12 | methoxy | Cl | Br | methyl |
| I-13 | methoxy | Cl | Br | n-propyl |
| I-14 | methoxy | Cl | Br | n-butyl |
| I-15 | methoxy | Cl | Br | benzyl |
| I-16 | methoxy | Cl | Br | 2-fluorobenzyl |
| I-17 | methoxy | methyl | H | methyl |
| I-18 | methoxy | methyl | Cl | methyl |
| I-19 | methoxy | methyl | H | n-propyl |
| I-20 | methoxy | methyl | H | n-butyl |
| I-21 | methoxy | methyl | H | benzyl |
| I-22 | methoxy | methyl | H | 2-fluorobenzyl |
| I-23 | methoxy | methyl | H | 3-fluorobenzyl |
| I-24 | methoxy | methyl | H | 4-fluorophenyl |
| I-25 | methoxy | methyl | H | 2-methylphenyl |
| I-26 | methoxy | methyl | H | 3-methylphenyl |
| I-27 | methoxy | methyl | H | 4-methylphenyl |
| I-28 | methoxy | methyl | Br | methyl |
| I-29 | methoxy | methyl | Br | n-propyl |
| I-30 | methoxy | methyl | Br | n-butyl |
| I-31 | methoxy | methyl | Br | benzyl |
| I-32 | methoxy | methyl | Br | 2-fluorobenzyl |
| I-33 | acetoxy | methyl | H | methyl |
| I-34 | acetoxy | methyl | Cl | methyl |
| I-35 | acetoxy | methyl | Br | methyl |
| I-36 | hydroxy | methyl | H | methyl |
| I-37 | hydroxy | methyl | Cl | methyl |
| I-38 | hydroxy | methyl | Br | methyl |
| I-39 | pivaloyloxy | methyl | H | methyl |
| I-40 | pivaloyloxy | methyl | Cl | methyl |
| I-41 | pivaloyloxy | methyl | Br | methyl |
| I-42 | Cl | Cl | H | methyl |
| I-43 | Cl | Cl | H | n-propyl |
| I-44 | Cl | Cl | H | n-butyl |
| I-45 | Cl | Cl | H | benzyl |
| I-46 | Cl | Cl | H | 2-fluorobenzyl |
| I-47 | Cl | Cl | H | 3-fluorobenzyl |
| I-48 | Cl | Cl | H | 4-fluorophenyl |
| I-49 | Cl | Cl | H | 2-methylphenyl |
| I-50 | Cl | Cl | H | 3-methylphenyl |
| I-51 | Cl | Cl | H | 4-methylphenyl |
| I-52 | Cl | Cl | Br | methyl |
| I-53 | Cl | Cl | Br | n-propyl |
| I-54 | Cl | Cl | Br | n-butyl |
| I-55 | Cl | Cl | Br | benzyl |
| I-56 | Cl | Cl | Br | 2-fluorobenzyl |
| I-57 | methyl | methyl | H | methyl |
| I-58 | methyl | methyl | H | n-propyl |
| I-59 | methyl | methyl | H | n-butyl |
| I-60 | methyl | methyl | H | benzyl |
| I-61 | methyl | methyl | H | 2-fluorobenzyl |
| I-62 | methyl | methyl | H | 3-fluorobenzyl |

TABLE 1-continued

| No. | R¹ | R² | R³ | R⁴ |
|---|---|---|---|---|
| I-63 | methyl | methyl | H | 4-fluorophenyl |
| I-64 | methyl | methyl | H | 2-methylphenyl |
| I-65 | methyl | methyl | H | 3-methylphenyl |
| I-66 | methyl | methyl | H | 4-methylphenyl |
| I-67 | methyl | methyl | Br | methyl |
| I-68 | methyl | methyl | Br | n-propyl |
| I-69 | methyl | methyl | Br | n-butyl |
| I-70 | methyl | methyl | Br | benzyl |
| I-71 | methyl | methyl | Br | 2-fluorobenzyl |

The formula II-x represents carbamates in which the combination of the substituents corresponds to one row of the table below:

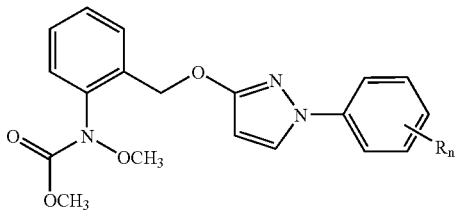

II-x

| No. | $R_n$ |
|---|---|
| II-1 | 2-F |
| II-2 | 3-F |
| II-3 | 4-F |
| II-4 | 2-Cl |
| II-5 | 3-Cl |
| II-6 | 4-Cl |
| II-7 | 2-Br |
| II-8 | 3-Br |
| II-9 | 4-Br |
| II-10 | 2-CH₃ |
| II-11 | 3-CH₃ |
| II-12 | 4-CH₃ |
| II-13 | 2-CF₃ |
| II-14 | 3-CF₃ |
| II-15 | 4-CF₃ |
| II-16 | 2,4-F₂ |
| II-17 | 2,4-Cl₂ |
| II-18 | 3,4-Cl₂ |
| II-19 | 2-Cl, 4-CH₃ |
| II-20 | 3-Cl, 4-CH₃ |

Preferred components b) are compounds of the formula II in which R is fluorine, chlorine, methyl or trifluoromethyl.

Likewise, particular preference is given to compounds of the formula II in which R is in the para-position; these compounds are described by the formula IIa:

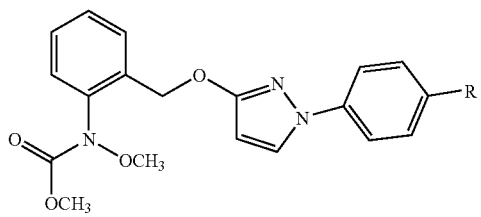

IIa

Preference is given to fungicidal mixtures which comprise, as component a), one of the compounds: I-33, I-35, I-42, I-44, I-46, I-60 or, preferably, I-18, I-28, I-37, and, as component b), one of the compounds: II-3, II-12, II-17 or, preferably, II-6, and, as component c), compounds III-a.

Owing to the basic character of their nitrogen atoms, the compounds II are capable of forming salts or adducts with inorganic or organic acids or with metal ions.

Examples of inorganic acids are hydrohalic acids, such as hydrogen fluoride, hydrogen chloride, hydrogen bromide and hydrogen iodide, carbonic acid, sulfuric acid, phosphoric acid and nitric acid.

Suitable organic acids are, for example, formic acid, carbonic acid [sic] and alkanoic acids, such as acetic acid, trifluoroacetic acid, trichloroacetic acid and propionic acid, and also glycolic acid, lactic acid, succinic acid, citric acid, benzoic acid, cinnamic acid, oxalic acid, p-toluenesulfonic acid, salicylic acid, p-aminosalicylic acid, 2-phenoxybenzoic acid or 2-acetoxybenzoic acid.

Suitable metal ions are in particular the ions of the elements of the first to eighth transition group, especially chromium, manganese, iron, cobalt, nickel, copper, zinc, and additionally those of the second main group, especially calcium and magnesium, and of the third and fourth main group, in particular aluminum, tin and lead. If appropriate, the metals can be present in the various valences that they can assume.

When preparing the mixtures, it is preferred to employ the pure active ingredients I, II and III, to which further active ingredients against harmful fungi or other pests, such as insects, arachnids or nematodes, or else herbicidal or growth-regulating active ingredients or fertilizers can be admixed.

The mixtures of the compounds I, II and III, or the compounds I, II and III used simultaneously, jointly or separately, exhibit outstanding activity against a wide range of phytopathogenic fungi, in particular from the classes of the Ascomycetes, Basidiomycetes, Phycomycetes and Deuteromycetes. Some of them act systemically and can therefore be employed as foliar- and soil-acting fungicides.

They are especially important for controlling a large number of fungi in a variety of crop plants, such as cotton, vegetable species (e.g. cucumbers, beans, tomatoes, potatoes and cucurbits), barley, grass, oats, bananas, coffee, maize, fruit species, rice, rye, soya, grapevine, wheat, ornamentals, sugar cane, and a variety of seeds.

They are particularly suitable for controlling the following phytopathogenic fungi: *Erysiphe graminis* (powdery mildew) in cereals, *Erysiphe cichoracearum* and *Sphaerotheca fuliginea* in cucurbits, *Podosphaera leucotricha* in apples, *Uncinula necator* in grapevines, *Puccinia* species in cereals, *Rhizoctonia* species in cotton, rice and lawns, *Ustilago* species in cereals and sugar cane, *Venturia inaequalis* (scab) in apples, *Helminthosporium* species in cereals, *Septoria nodorum* in wheat, *Botrytis cinera* (gray mold) in strawberries, vegetables, ornamentals and grapevines, *Cercospora arachidicola* in groundnuts, *Pseudocercosporella herpotrichoides* in wheat and barley, *Pyricularia oryzae* in rice, *Phytophthora infestans* in potatoes and tomatoes, *Plasmopara viticola* in grapevines, *Pseudoperonospora* species in hops and cucumbers, *Alternaria* species in vegetables and fruit, *Mycosphaerella* species in bananas and *Fusarium* and *Verticillium* species.

They can furthermore be employed in the protection of materials (for example the protection of wood), for example against Paecilomyces variotii.

The compounds I, II and III can be applied simultaneously, that is either together or separately, or successively, the sequence, in the case of separate application, generally not having any effect on the result of the control measures.

In the mixtures, the compounds I, II and III are employed such that the respective mixing ratios of the compounds I and II, I and III and II and III are in each case from 20:1 to 1:20 and in particular from 10:1 to 1:10.

Depending on the kind of effect desired, the application rates of the mixtures according to the invention are, in particular in agricultural crop areas, from 0.01 to 8 kg/ha, preferably 0.1 to 5 kg/ha, in particular 0.1 to 3.0 kg/ha.

The application rates of the compounds I are from 0.005 to 5 kg/ha, preferably 0.08 to 3 kg/ha, in particular 0.06 to 2.0 kg/ha.

Correspondingly, in the case of the compounds II, the application rates are from 0.005 to 3 kg/ha, preferably 0.02 to 2 kg/ha, in particular 0.04 to 1.0 kg/ha.

For the compounds III, the application rates are correspondingly from 0.01 to 2 kg/ha and preferably from 0.05 to 1 kg/ha.

For seed treatment, the application rates of the mixture are generally from 0.001 to 250 g/kg of seed, preferably 0.01 to 100 g/kg, in particular 0.01 to 50 g/kg.

If phytopathogenic harmful fungi are to be controlled, the separate or joint application of the compounds I, II and, if appropriate, III or of the mixtures of the compounds I, II and, if appropriate, III is effected by spraying or dusting the seeds, the plants or the soils before or after sowing of the plants, or before or after plant emergence.

The fungicidal synergistic mixtures according to the invention or the compounds I, II and, if appropriate, III can be formulated for example in the form of ready-to-spray solutions, powders and suspensions or in the form of highly concentrated aqueous, oily or other suspensions, dispersions, emulsions, oil dispersions, pastes, dusts, materials for broadcasting or granules, and applied by spraying, atomizing, dusting, broadcasting or watering. The use form depends on the intended purpose; in any case, it should ensure as fine and uniform as possible a distribution of the mixture according to the invention.

The formulations are prepared in a known manner, e.g. by adding solvents and/or carriers. The formulations are usually admixed with inert additives, such as emulsifiers or dispersants.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenyl ether, ethoxylated isooctyl, octyl- or nonylphenol, alkylphenol or tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene [lacuna], lauryl alcohol polyglycol ether acetate, sorbitol esters, lignosulfite waste liquors or methylcellulose.

Powders, materials for broadcasting and dusts can be prepared by mixing or jointly grinding the compounds I, II or III or the mixture of the compounds I, II and III with a solid carrier.

Granules (e.g. coated granules, impregnated granules or homogeneous granules) are usually prepared by binding the active compound, or active compounds, to a solid carrier.

Fillers or solid carriers are, for example, mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials and fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The formulations generally comprise from 0.1 to 95% by weight, preferably 0.5 to 90% by weight, of one of the compounds I or II [lacuna] or of the mixture of the compounds I, II and, if appropriate, III. The active compounds are employed in a purity of from 90% to 100%, preferably 95% to 100% (according to NMR spectrum or HPLC).

The compounds I, II and III, the mixtures, or the corresponding formulations, are applied by treating the harmful fungi, their habitat, or the plants, seeds, soils, areas, materials or spaces to be kept free from them with a fungicidally effective amount of the mixture, or of the compounds I, II and III in the case of separate application.

Application can be effected before or after infection by the harmful fungi.

USE EXAMPLE

The synergistic activity of the mixtures according to the invention was demonstrated by the following experiments:

The active compounds, separately or together, were formulated as a 10% emulsion in a mixture of 63% by weight of cyclohexanone and 27% by weight of emulsifier, and diluted with water to the desired concentration.

Evaluation was carried out by determining the infected leaf areas in percent. These percentages were converted into efficacies. The efficacy (W) was calculated as follows using Abbot's formula:

$$W=(1-\alpha)\cdot 100/\beta$$

α corresponds to the fungal infection of the treated plants in % and

β corresponds to the fungal infection of the untreated (control) plants in %

An efficacy of 0 means that the infection level of the treated plants corresponds to that of the untreated control plants; an efficacy of 100 means that the treated plants were not infected.

The expected efficacies of the mixtures of the active compounds were determined using Colby's formula [R. S. Colby, Weeds 15, 20–22 (1967)] and compared with the observed efficacies.

$$\text{Colby's formula: } E=x+y-x\cdot y/100$$

E expected efficacy, expressed in % of the untreated control, when using the mixture of the active compounds A and B at the concentrations a and b x efficacy, expressed in % of the untreated control, when using active compound A at a concentration of a y efficacy, expressed in % of the untreated control, when using active compound B at a concentration of b.

Use Example 1

Protective Activity Against Mildew of Wheat Caused by *Erysiphe* [syn. *Blumeria*] *graminis* forma specialis *tritici*

Leaves of potted wheat seedlings of the cultivar "Kanzler" were sprayed to runoff point with an aqueous preparation of active compound which had been prepared from a stock solution made of 10% of active compound, 85% of cyclohexanone and 5% of emulsifier and, 24 hours after the spray coating had dried on, dusted with spores of mildew of wheat (*Erysiphe* [syn. *Blumeria*] *graminis* forma specialis. *tritici*). The test plants were then placed in a greenhouse at 20–24° C. and 60–90% relative atmospheric humidity. After 7 days, the extent of the mildew development was determined visually in % infection of the total leaf area.

The visually determined percentages of infected leaf area were converted into efficacies as % of the untreated control. An efficacy of 0 means that the infection level of the treated plants corresponds to that of the untreated control; an efficacy of 100 means 0% infection. The expected efficacies of the combinations of active compounds were determined using Colby's formula (Colby, S. R. (Calculating synergistic and antagonistic responses of herbicide Combinations", Weeds, 15, pp. 20–22, 1967) and compared with the observed efficacies.

TABLE 1

| Active compound | Concentration of active compound in the spray liquor in ppm | Efficacy in % of the untreated control |
|---|---|---|
| Control (untreated) | (94% infection) | 0 |
| Compound I-28 | 0.25 | 79 |
|  | 0.125 | 57 |
|  | 0.06 | 36 |
| Compound I-37 | 0.25 | 79 |
|  | 0.125 | 57 |
|  | 0.06 | 36 |
| Compound II-6 = pyraclostrobin | 2.5 | 57 |
|  | 1.25 | 47 |
|  | 0.6 | 36 |
| Compound II-12 | 2.5 | 57 |
|  | 1.25 | 25 |
|  | 0.6 | 25 |
| Compound III.a = epoxiconazole | 1.25 | 4 |
|  | 0.6 | 4 |
|  | 0.3 | 4 |

Two-compound mixtures

| Binary combination | Observed efficacy | Calculated efficacy*) |
|---|---|---|
| Compound I-28 + compound II-6 0.125 + 1.25 ppm (1:10) = Mixture A | 89 | |
| Compound I-28 + compound II-6 0.06 + 0.6 ppm (1:10) = Mixture B | 79 | |
| Compound I-28 + compound II-6 0.125 + 0.6 ppm (1:5) = Mixture C | 89 | |
| Compound I-28 + compound II-6 0.25 + 1.25 ppm (1:5) = Mixture D | 89 | |
| Compound I-28 + compound II-12 0.125 + 1.25 ppm (1:10) = Mixture E | 84 | |
| Compound I-28 + compound II-12 0.06 + 0.6 ppm (1:10) = Mixture F | 79 | |
| Compound I-28 + compound II-12 0.25 + 1.25 ppm (1:5) = Mixture G | 84 | |

TABLE 1-continued

| Compound I-28 + compound II-12 0.125 + 0.6 ppm (1:5) = Mixture H | 89 | |
|---|---|---|
| Compound I-37 + compound II-6 0.125 + 1.25 ppm (1:10) = Mixture I | 89 | |
| Compound I-37 + compound II-6 0.06 + 0.6 ppm (1:10) = Mixture J | 79 | |
| Compound I-37 + compound II-6 0.25 + 1.25 ppm (1:5) = Mixture K | 89 | |
| Compound I-37 + compound II-6 0.125 + 0.6 ppm (1:5) = Mixture L | 79 | |
| Compound I-37 + compound II-12 0.125 + 1.25 ppm (1:10) = Mixture M | 84 | |
| Compound I-37 + compound II-12 0.06 + 0.6 ppm (1:10) = Mixture N | 73 | |
| Compound I-37 + compound II-12 0.25 + 1.25 ppm (1:5) = Mixture O | 89 | |
| Compound I-37 + compound II-12 0.125 + 0.6 ppm (1:5) = Mixture P | 84 | |

TABLE 2

Three-compound mixtures

| Ternary combinations according to the invention | Observed efficacy | Calculated efficacy*) |
|---|---|---|
| Compound I-28 + compound II-6 + compound III.a 0.125 + 1.25 + 1.25 ppm (1:10:10) Mixture A + 1.25 ppm III.a | 100 | 90 |
| Compound I-28 + compound II-6 + compound III.a 0.06 + 0.6 + 0.6 ppm (1:10:10) Mixture B + 0.6 ppm III.a | 97 | 80 |
| Compound I-28 + compound II-6 + compound III.a 0.125 + 0.6 + 0.6 ppm (1:5:5) Mixtur C + 0.6 ppm III.a | 100 | 89 |
| Compound I-28 + compound II-6 + compound III.a 0.125 + 0.6 + 0.3 ppm (1:5:2.5) Mixture C + 0.3 ppm III.a | 97 | 90 |
| Compound I-28 + compound II-6 + compound III.a | 100 | 90 |

TABLE 2-continued

Three-compound mixtures

| Ternary combinations according to the invention | Observed efficacy | Calculated efficacy*) |
|---|---|---|
| Compound I-28 + compound II-12 + compound III.a<br>0.25 + 1.25 + 1.25 ppm<br>(1:5:5)<br>Mixture D + 1.25 ppm III.a | 100 | 85 |
| Compound I-28 + compound II-12 + compound III.a<br>0.125 + 1.25 + 1.25 ppm<br>(1:10:10)<br>Mixture E + 1.25 ppm III.a | 89 | 80 |
| Compound I-28 + compound II-12 + compound III.a<br>0.06 + 0.6 + 0.6 ppm<br>(1:10:10)<br>Mixture F + 0.6 ppm III.a | 100 | 85 |
| Compound I-28 + compound II-12 + compound III.a<br>0.25 + 1.25 + 1.25 ppm<br>(1:5:5)<br>Mixture G + 1.25 ppm III.a | 100 | 85 |
| Compound I-28 + compound II-12 + compound III.a<br>0.25 + 1.25 + 0.6 ppm<br>(1:5:2.4)<br>Mixture G + 0.6 ppm III.a | 100 | 89 |
| Compound I-28 + compound II-12 + compound III.a<br>0.125 + 0.6 + 0.6 ppm<br>(1:5:5)<br>Mixture H + 0.6 ppm III.a | 100 | 90 |
| Compound I-37 + compound II-6 + compound III.a<br>0.125 + 1.25 + 1.25 ppm<br>(1:10:10)<br>Mixture I + 1.25 ppm III.a | 100 | 90 |
| Compound I-37 + compound II-6 + compound III.a<br>0.06 + 0.6 + 0.6 ppm<br>(1:10:10)<br>Mixture J + 0.6 ppm III.a | 93 | 80 |
| Compound I-37 + compound II-6 + compound III.a<br>0.25 + 1.25 + 1.25 ppm<br>(1:5:5)<br>Mixture K + 1.25 ppm III.a | 100 | 90 |
| Compound I-37 + compound II-6 + compound III.a<br>0.25 + 1.25 + 0.6 ppm<br>(1:5:2.5)<br>Mixture K + 0.6 ppm III.a | 100 | 90 |
| Compound I-37 + compound II-6 + compound III.a<br>0.125 + 0.6 + 0.6 ppm<br>(1:5:5)<br>Mixture L + 0.6 ppm III.a | 100 | 79 |
| Compound I-37 + compound II-6 + compound III.a<br>0.125 + 0.6 + 0.3 ppm<br>(1:5:2.5)<br>Mixture L + 0.3 ppm III.a | 97 | 80 |
| Compound I-37 + compound II-12 + compound III.a<br>0.125 + 1.25 + 1.25 ppm<br>(1:10:10)<br>Mixture M + 1.25 ppm III.a | 100 | 85 |
| Compound I-37 + compound II-12 + compound III.a<br>0.06 + 0.6 + 0.6 ppm<br>(1:5:5)<br>Mixture N + 0.6 ppm III.a | 88 | 74 |
| Compound I-37 + compound II-12 + compound III.a<br>0.25 + 1.25 + 1.25 ppm<br>(1:5:5)<br>Mixture O + 1.25 ppm III.a | 100 | 90 |
| Compound I-37 + compound II-12 + compound III.a<br>0.25 + 1.25 + 0.6 ppm<br>(1:5:2.5)<br>Mixture O + 0.6 ppm III.a | 100 | 90 |
| Compound I-37 + compound II-12 + compound III.a<br>0.125 + 0.6 + 0.6 ppm<br>(1:5:5)<br>Mixture P + 0.6 ppm III.a | 100 | 84 |
| Compound I-37 + compound II-12 + compound III.a<br>0.125 + 0.6 + 0.3 ppm<br>(1:5:2.5)<br>Mixture P + 0.3 ppm III.a | 97 | 85 |

*)calculated using Colby's formula

The test results show that the observed efficacy for the three-compound mixtures (ternary mixtures) is higher than the efficacy calculated for the two-compound mixtures (binary mixtures) (from Synerg 167B. XLS) using Colby's formula.

We claim:
1. A fungicidal mixture, comprising
a) a benzophenone of the formula I,

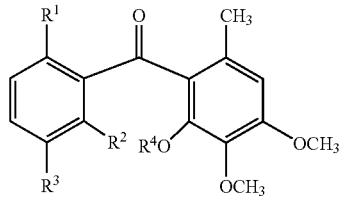

in which
R¹ is chlorine, methyl, methoxy, acetoxy, pivaloyloxy or hydroxyl;
R² is chlorine or methyl;
R³ is hydrogen, halogen or methyl; and
R⁴ is $C_1$–$C_6$-alkyl. and
b) a carbamate of the formula II,

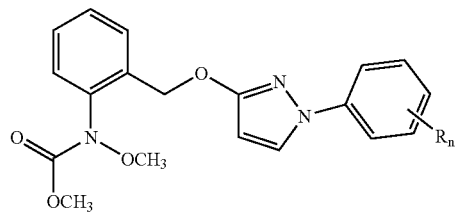

in which n is 1 or 2 and R is halogen, $C_1$–$C_4$-alkyl or $C_1$–$C_2$-haloalkyl, where the radicals R may be different if n is 2, and
c) an azole derivative III selected from the group of the compounds III.a to III.e:
(2RS,3SR)-1-[3-(2-chlorophenyl)-2-(4-fluorophenyl)-oxiran-2-ylmethyl]-1H-1,2,4-triazole

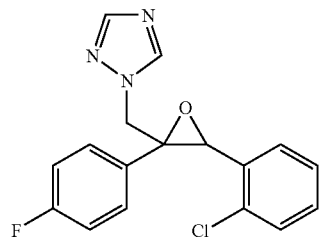

(1RS,5RS;1RS,5SR)-5-(4-chlorobenzyl)-2,2-dimethyl-1-(1H-1,2,4-triazol-1-ylmethyl)cyclopentanol

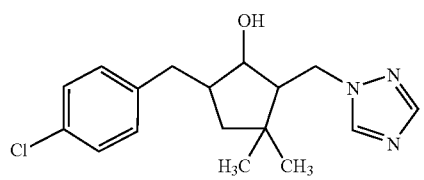

(R,S)-1-[2-(2,4-dichlorophenyl)-4-propyl-1,3-dioxolan-2-yl-methyl]-1H-1,2,4-triazole

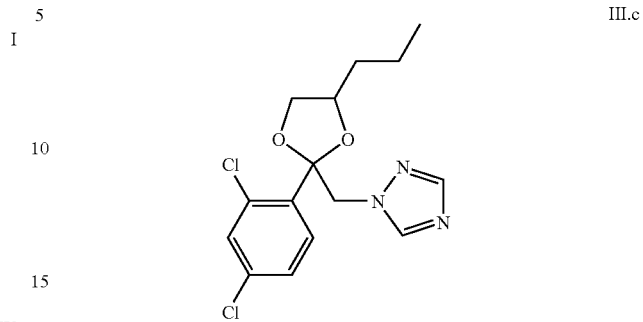

(R,S)-1-(4-chlorophenyl)-4,4-dimethyl-3-(1H-1,2,4-triazol-1-ylmethyl)pentan-3-ol

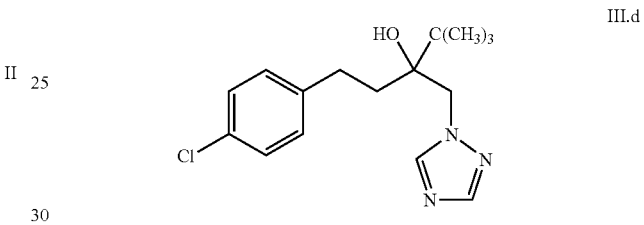

(R,S)-1-(2-chlorophenyl)-2-(1-chlorocyclopropyl)-3-(5-mercapto-1H-1,2,4-triazolyl)propan-2-ol

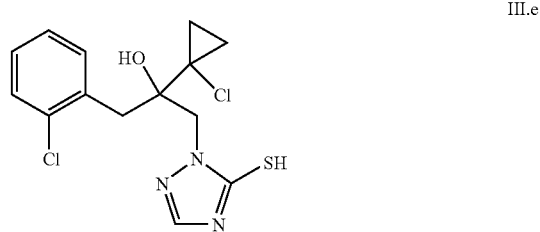

in a synergistically effective amount.
2. A fungicidal mixture as claimed in claim 1, where in formula I
R¹ is methoxy, acetoxy or hydroxyl;
R² is methyl;
R³ is hydrogen, chlorine or bromine; and
R⁴ is $C_1$–$C_4$-alkyl.
3. A fungicidal mixture as claimed in claim 1, where the carbamate II corresponds to formula IIa,

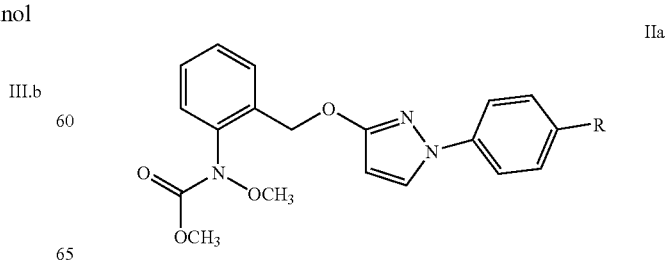

in which R is fluorine, chlorine or methyl.

4. A fungicidal mixture as claimed in claim 1, where the azole derivative III.a is used.

5. A fungicidal mixture as claimed in claim 1, wherein the weight ratio of the compounds I and II, I and III and II and III is in each case from 20:1 to 1:20.

6. A method for controlling harmful fungi, which comprises treating the harmful fungi, their habitat or the plants, seeds, soils, areas, materials or spaces to be kept free from them with a fungicidal mixture as claimed in claim 1.

7. A method as claimed in claim 6, wherein the benzophenones of the formula I are applied in an amount of from 0.08 to 3 kg/ha.

8. A method as claimed in claim 6, wherein the carbamates of the formula II are applied in an amount of from 0.02 to 2 kg/ha.

9. A method as claimed in any of claims 6, wherein the azole derivatives of the formula III are applied in an amount of from 0.01 to 2 kg/ha.

* * * * *